United States Patent [19]

Fulcher

[11] Patent Number: 4,673,581

[45] Date of Patent: Jun. 16, 1987

[54] FRIED FOOD PRODUCT FRIED IN SYNTHETIC COOKING OILS CONTAINING DICARBOXYLIC ACID ESTERS

[75] Inventor: John Fulcher, Dallas, Tex.

[73] Assignee: Frito-Lay, Inc., Dallas, Tex.

[21] Appl. No.: 812,752

[22] Filed: Dec. 23, 1985

Related U.S. Application Data

[62] Division of Ser. No. 598,063, Apr. 4, 1984, Pat. No. 4,582,927.

[51] Int. Cl.$^4$ .......................... A23L 1/01; A23L 1/307
[52] U.S. Cl. .................................... 426/531; 426/612; 426/438; 426/523; 426/804
[58] Field of Search ............... 426/611, 612, 438, 531, 426/523, 804

[56] References Cited

U.S. PATENT DOCUMENTS 3,600,186  8/1971  Mattson et al. ...................... 426/611
3,963,699  6/1976  Rizzi et al. ...................... 426/611 X
4,508,746  4/1985  Hamm .............................. 426/611 X Primary Examiner—Robert Yoncoskie
Attorney, Agent, or Firm—Bernard, Rothwell & Brown

[57] ABSTRACT

Diesters of the formula

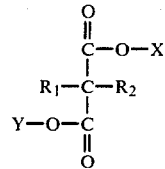

wherein $R_1$ and $R_2$ are hydrogen or alkyl of from 1 to about 20 carbon atoms, and X and Y are alkyl, alkenyl or dienyl of from about 12 to about 18 carbon atoms, useful as low calorie synthetic oils suitable for consumption by mammals.

7 Claims, No Drawings

FRIED FOOD PRODUCT FRIED IN SYNTHETIC COOKING OILS CONTAINING DICARBOXYLIC ACID ESTERS

This is a division of application Ser. No. 598,063, filed Apr. 4, 1984 now U.S. Pat No. 4,582,927.

FIELD OF THE INVENTION

The present invention relates to the synthesis and use of synthetic oils as substitutes for animal and vegetable fats and oils in the preparation of foods for human and animal consumption.

BACKGROUND OF THE INVENTION

Lipids (fats and oils) constitute between 30 and 40% of the caloric intake of the average American diet. Dietary fat, consisting of triglycerides, is digested to free fatty acids and monoglycerides, primarily in the small intestine. The α-lipase steapsin cleaves the glycerol esters at the 1- and 3- positions. Fatty acids of 6 to 10 carbons and unsaturated fatty acids are rapidly absorbed, while those of 12 to 18 carbons are absorbed more slowly. Absorption of the β-monoglycerides by the mucosa of the small intestine results in a final digestion and absorption of up to 95% of the total dietary fat. Since fats yield about twice the energy per gram of either carbohydrates or proteins, substitution of a non-digestible material for a portion of the normal dietary fat offers a painless and effective method for control of obesity, hypertension, and other diseases associated with excessive caloric intake.

There is considerable evidence that steapsin is an enzyme which is specific for esters of 1, 3-diols and glycerol. U.S. Pat. No. 2,962,419 to Minich describes in vitro tests of pentaerythretol tetracaprylate to demonstrate that there is no hydrolysis of the pentaerythritol ester by pancreatic lipase (steapsin) and a greatly diminished total serum lipid concentration when the substance was used in place of fat in a typical rat diet. Canadian Pat. No. 1,106,681 to Trost describes the feeding of dialkyl glycerol ethers to rats, concluding that the esters were generally non-digestible, and tests of sucrose polyester in obese human volunteers showed decreased total plasma cholesterol and plasma triglycerides (Glueck et al., Am. J. Cli. Nutri., 35, 1352 (1982)). U.S. Pat. No. 3,600,186 to Mattson et al. describe the use of fatty acid ester compounds having at least 4 fatty acid ester groups for use as triglyceride fat substitutes.

Esters of malonic acid and dialkyl malonic acid, and low molecular weight alcohols are known but are unsuitable for use as vegetable oil substitutes due to their low boiling points.

There remains a need for stable synthetic oils which are not readily digestible in mammals, and which are suitable for use in the production of low calorie fried and baked products containing starches, and in other foods such as oleomargarine, salad oil and other foods normally containing vegetable oils.

SUMMARY OF THE INVENTION

The invention provides esters of the formula

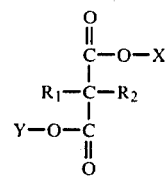

wherein $R_1$ and $R_2$ are hydrogen or alkyl radicals containing from 1 to about 20 carbon atoms, and X and Y are alkyl, alkenyl or dienyl radicals containing from about 12 to about 18 carbon atoms. These materials are synthetic oils and low melting solids which are hydrolyzed slowly or not at all, by pancreatic lipase. Food products made with or fried in these synthetic oils contain less metabolizable lipids and are, therefore, lower in available calories, making them suitable for use by persons with weight or some lipid control difficulties.

DETAILED DESCRIPTION OF THE INVENTION

The synthetic edible oils of the present invention are represented by the formula:

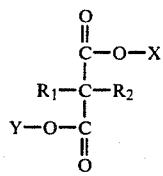

wherein $R_1$ and $R_2$, which may be the same or different, are hydrogen or alkyl radicals of from 1 to about 20 carbon atoms, e.g., methyl, ethyl, hexadecyl, eicosyl, and the like; and X and Y, which may be the same or different, are alkyl, alkenyl or dienyl radicals of from about 12 to about 18 carbon atoms, e.g., dodecyl, octadecyl, dodecenyl, oleyl, linoleyl, and the like.

In preferred compounds, at least one of the R groups is an alkyl of from 1 to about 20 carbon atoms, the other R group being hydrogen or a similar alkyl. In particularly preferred compounds, one of the R groups is hydrogen and the other is an alkyl of about 16 carbon atoms, or both R groups are alkyls of about 16 carbon atoms.

The radicals X and Y are preferably alkyls of from about 14 to about 18 carbon atoms, or alkenyls or dienyls of about 18 carbon atoms.

Particularly preferred compounds are hexadecyl dioleylmalonate and dihexadecyl dioleylmalonate.

The compounds of this invention are synthetic organic compounds which display the physical properties of animal fats and vegetable oils. They are liquid or solid at room temperature, depending upon molecular weight and structure, and oils at normal cooking temperatures. Unlike naturally-occurring fats and oils, which are triglycerides (fatty acid esters of glycerol) the products of this invention are fatty alcohol derivatives of malonic acid, and mono- and dialkyl malonic acid. Unlike triglycerides, these compounds resist hydrolysis by pancreatic lipase and other components of the digestive juices present in the stomach and small intestine. As a result, most of the material is not absorbed by the small intestine.

Examples of fatty alcohols suitable for the practice of this invention include oleyl, myristic, linoleic, palmitic and stearic alcohols, with oleyl alcohol being particularly preferred. They are readily available commercially, and readily synthesized by reduction of the corresponding fatty acid obtained by the saponification of fats and oils. Suitable acids include malonic acid, monoalkyl and dialkyl malonic acid, such as hexadecyl malonic acid and dihexadecyl malonic acid. Both the pure, symmetric diesters and mixed esters are suitable, analogous to the mixed esters in naturally-occurring fats and oils.

The synthesis of the compounds of this invention may be accomplished by several pathways. For example, certain compounds of the invention may be prepared by reacting a malonyl dihalide with a fatty alcohol or a mixture of fatty alcohols. If desired, the product may then be reacted with an alkyl halide, or a mixture of alkyl halides, in a basic solution to produce a product of higher molecular weight with a correspondingly higher melting point and boiling point.

Impurities may be removed from the esters formed by the above procedures by various distillation or silica gel chromatography using conventional equipment and techniques familiar to those experienced in the chemical arts.

The lower molecular weight compounds of the present invention are suitable as substitutes for natural oils in spreads such as mayonnaise and margarine, and other food products which are not subjected to high temperatures for long periods of time. Higher molecular weight compounds are preferred for use as synthetic frying oils.

The synthetic oils of the present invention may also comprise mixtures of the disclosed compounds.

Particularly preferred synthetic oils of the present invention have a melting point below about 10° C., a boiling point above about 230° C., are absorbed by the small intestine of a mammal at a substantially lower rate than corn oil, and/or provide substantially fewer calories than corn oil when consumed by a mammal.

Food products fried in synthetic oils of the present invention have a lower metabolic fat content than a similar product cooked in animal fat or vegetable oil. Similarly, food products in which their normal content of animal fat or vegetable oil as been partially or completely substituted by the synthetic oils of this invention have a lower metabolic fat content than similar products not containing synthetic oil.

The invention is further illustrated by the following example, which is not intended to be limiting.

EXAMPLE 1

Preparation of Hexadecyl Dioleylmalonate and Dihexadecyl Dioleylmalonate

Three molar equivalents of 1-bromohexadecane (available from Fluka Chemical Corporation), one molar equivalent of dioleylmalonate (prepared by the reaction of malonyl dichloride (Aldrich) with oleyl alcohol (Aldrich)), 0.1 molar equivalent of tetra-n-butylammonium hydroxide (40% solution in water (Aldrich)), and 2-3 molar equivalents of potassium hydroxide (50% solution in water) were combined in a flask with a small amount of water and stirred 2-4 hours at room temperature (20°-25° C.).

Stirring for two hours with two molar equivalents of potassium hydroxide resulted in a mixture containing approximately 67% hexadecyl dioleylmalonate and 33% dihexadecyl dioleylmalonate. Stirring for four hours with three molar equivalents potassium hydroxide gave a higher proportion (67%) of dihexadecyl dioleylmalonate. The two malonic esters were purified by removal of the aqueous phase by extraction with water, vacuum distillation to remove unreacted bromohexadecane and oleyl alcohol byproduct, and silica gel chromatography using petroleum ether.

The dihexadecyl dioleylmalonate was distinguished by its higher melting point (36°-37° C.), quaternary carbon nmr signal at 56 ppm and molecular ion (1054). The hexadecyl dioleylmalonate had a melting point of 28°-29° C., tertiary carbon nmr signal at 52 ppm, and molecular ion (829).

What is claimed is:

1. A food product fried in a synthetic edible oil comprising a mixture of hexadecyl dioleylmalonate and dihexadecyl dioleylmalonate.

2. A fried food product which has been fried in a synthetic edible oil comprising one or more compounds of the formula

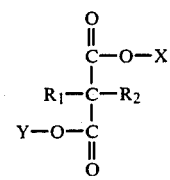

wherein $R_1$ and $R_2$, which may be the same or different, are hydrogen or alkyl of from 1 to about 20 carbon atoms, with the proviso that at least one of the R groups, $R_1$ or $R_2$, is an alkyl from 1 to 20 carbon atoms, X is an alkyl, alkenyl or dienyl radical of from about 12 to about 18 carbon atoms and Y is an alkenyl or dienyl radical of from about 12 to about 18 carbon atoms.

3. The food product of claim 2 with a lower metabolic fat content than a product cooked in animal fat or vegetable oil.

4. The food product of claim 2 fried in a hexadecyl dioleylmalonate.

5. The food product of claim 2 fried in dihexadecyl dioleylmalonate.

6. A food product containing the synthetic edible oil of claim 2.

7. A method of frying food comprising heating the synthetic edible oil of claim 2 to frying temperature and contacting a food with said synthetic edible oil for a time sufficient to fry said food.

* * * * *